US010030223B2

(12) United States Patent
Kim et al.

(10) Patent No.: US 10,030,223 B2
(45) Date of Patent: Jul. 24, 2018

(54) APPARATUS AND METHOD FOR SIMULTANEOUS OPERATION OF REFINING CELLULOSIC BIOMASS AND MIXING ENZYMES

(71) Applicants: SK Innovation Co., LTD., Seoul (KR); SK Energy Co., LTD., Seoul (KR)

(72) Inventors: Taewan Kim, Daejeon (KR); Bonwook Koo, Daejeon (KR); Minsu Koo, Daejeon (KR)

(73) Assignees: SK Innovation Co., Ltd., Seoul (KR); SK Energy Co., Ltd., Seoul (KR)

( * ) Notice: Subject to any disclaimer, the term of this patent is extended or adjusted under 35 U.S.C. 154(b) by 312 days.

(21) Appl. No.: 14/683,053

(22) Filed: Apr. 9, 2015

(65) Prior Publication Data
US 2015/0291928 A1    Oct. 15, 2015

(30) Foreign Application Priority Data

Apr. 9, 2014    (KR) .................. 10-2014-0042621

(51) Int. Cl.
*C12M 1/00*    (2006.01)
*C12M 1/33*    (2006.01)
(Continued)

(52) U.S. Cl.
CPC ............ *C12M 45/02* (2013.01); *C12M 21/12* (2013.01); *C12M 45/09* (2013.01); *C12M 45/20* (2013.01);
(Continued)

(58) Field of Classification Search
CPC ...................................................... D21D 1/30
See application file for complete search history.

(56) References Cited

U.S. PATENT DOCUMENTS 3,790,092 A * 2/1974 Reinhall .................. D21D 1/30
241/244
3,942,729 A * 3/1976 Fredriksson ............. D21D 1/30
241/250
(Continued)

FOREIGN PATENT DOCUMENTS

JP            3417802 B2    6/2003
WO    2013/072558 A1    5/2013

OTHER PUBLICATIONS

Office Action dated Jun. 13, 2016 of corresponding Korean Patent Application No. 10-2015-0034397—7 pages.

*Primary Examiner* — William H. Beisner
(74) *Attorney, Agent, or Firm* — The Webb Law Firm

(57) ABSTRACT

An apparatus comprises: a hopper for feeding biomass; a horizontal extruder comprising a cylindrical housing and a rotatable screw mounted in the housing, in which one side of the housing is connected to the hopper, and an outlet provided at the other side of the housing is connected to an inlet for feeding biomass into a refiner; and a refiner comprising a stator disc having a cooling water space formed on the outer peripheral surface thereof, one or more enzyme feeding holes provided in a refining region adjacent to the circumference of the stator disc, and a biomass inlet provided at the central portion thereof, and a refining disc which is disposed so as to form a gap with the inner surface of the stator disc and to have a refining region opposite to that of the stator disc and is rotated by a separate motor.

7 Claims, 2 Drawing Sheets

(51) Int. Cl.
*C12P 19/14* (2006.01)
*C12P 19/02* (2006.01)
*D21D 1/30* (2006.01)
*C12P 7/10* (2006.01)

(52) U.S. Cl.
CPC .............. *C12P 19/02* (2013.01); *C12P 19/14* (2013.01); *D21D 1/30* (2013.01); *C12P 7/10* (2013.01); *Y02E 50/17* (2013.01)

(56) References Cited

U.S. PATENT DOCUMENTS

| | | | |
|---|---|---|---|
| 4,129,263 A | | 12/1978 | Sjobom |
| 5,314,583 A | * | 5/1994 | Kappel .................. B02C 23/34 162/25 |
| 2010/0317053 A1 | * | 12/2010 | Stromberg .......... B01F 7/00766 435/41 |

* cited by examiner

APPARATUS AND METHOD FOR SIMULTANEOUS OPERATION OF REFINING CELLULOSIC BIOMASS AND MIXING ENZYMES

TECHNICAL FIELD

The present disclosure relates to an apparatus and method for refining biomass simultaneously with mixing biomass with an enzyme.

BACKGROUND ART

Bioethanol was already commercialized in Brazil and the USA, and the production thereof is greatly increasing. However, it is produced from food biomass such as sugar canes or corn, and causes the instability of crop prices. Because an increase in the price of crops leads directly to an increase in the price of bioethanol, it can increase the fuel price and even can cause problems associated with fuel supply. For this reason, studies and investments on a variety of non-food biomass alternatives have been continued, and among them, woody biomass is a representative alternative.

Woody biomass (trees, grasses, agricultural residues such as rice straw and chaff, etc.) together with sugar biomass (sugar canes, sugar beets, etc.) and starch biomass (crops, potatoes, etc.) are used as biofuels that can produce energy such as methane, ethanol and hydrogen by pyrolysis and fermentation processes.

Woody biomass is generally composed of cellulose (40-50%), hemicellulose (25-35%) and lignin (15-20%), even though the compositions and contents of the chemical components of wood vary depending on the kind of tree (a needle-leaf tree or a broad-leaved tree), the age of trees, etc. Cellulose is a polymer compound consisting of glucose units regularly linked by hydrogen bonds and van der Waals forces, and hemicellulose is composed of pentoses, such as xylose and arabinose, linked in the β-1,4 configuration, and serves as an interface between cellulose and lignin. Also, lignin is an insoluble, non-degradable polymer compound with aromatic substances having phenylpropanoid units linked together irregularly, and is characterized by a structure that blocks the degradation of polysaccharides.

A technology of producing biofuels from woody biomass or perennial grassy biomass entails a problem in that the production cost of biofuels is increased due to a relatively high lignin content compared to that of starch (crop) biomass and sugar (sugar cane liquor) biomass.

Biofuel production processes of preparing bioethanol from cellulose are grossly divided into feedstock acquisition, pretreatment, saccharification, fermentation and purification processes. Particularly, the pretreatment process is performed when non-degradable woody biomass composed of cellulose, hemicellulose and lignin, linked in a complex and hard form, is used. The pretreatment process aims to effectively separate cellulose and hemicellulose from lignin having a complex and hard structure, and the separated cellulose is hydrolyzed into glucose, a representative monosaccharide, by microorganisms or enzyme in the saccharification process. When glucose is fermented, ethanol is produced.

As the pretreatment methods, many physical and chemical methods have been studied, including steam explosion, alkaline treatment, sulfur dioxide treatment, hydrogen peroxide treatment, supercritical ammonia treatment, ammonia freeze explosion, ammonia recycled percolation, and pyrochemical treatment methods.

The physical methods typically include milling and steam explosion. Milling is a method that grinds lignocellulosic particles into very fine particles by a milling device to induce the structural change of the lignocellulosic particles, and has disadvantages in that it consumes a large amount of energy and has low yield or saccharification rate. The steam explosion method is a method in which lignocellulose is steamed in an autoclave containing high-temperature steam for a certain time, and then the valve of the autoclave is instantaneously opened so that the structure of the lignocellulose is instantaneously opened, like popcorn, thereby providing a substrate with which an enzyme can easily come into contact.

The chemical methods typically include a method of treating lignocellulose with 2% (w/w) or less sulfuric acid, and a dilute-acid hydrolysis method in which lignocellulose is steamed with high-temperature steam at a temperature of 160~200° C. for 1-10 minutes, like the steam explosion method, so that hemicellulose is hydrolyzed into monosaccharides and oligosaccharides by an acid catalytic reaction.

The physical pretreatment method has disadvantages in that the process proceeds slowly, a large amount of energy is consumed, and saccharification efficiency and economic efficiency are low. Also, the chemical pretreatment method has disadvantages in that, because a strongly acidic or strongly alkaline compound is used, a portion of pentose produced is decomposed into furfural acting as a fermentation inhibitor, and in that it is costly, is unsuitable for treatment of a large amount of lignocellulose, is toxic, corrodes equipment, and causes environmental pollution problems by waste.

U.S. Pat. No. 4,129,263 discloses an apparatus configured to refine biomass by feeding biomass between two rotating discs. Japanese Patent No. 3417802 discloses an apparatus configured to refine feedstock by feeding the feedstock between two rotating discs.

The discussion in the foregoing background section is to provide general background information, and does not constitute an admission of prior art.

SUMMARY

One aspect of the present invention provides an enzyme mixing-biomass refining apparatus, which can simultaneously perform biomass refining and enzyme mixing using a refiner including a stator disc having one or more enzyme feeding holes formed thereon.

Another aspect of the present invention provides a method for simultaneously performing biomass refining and enzyme mixing using the above-described refiner.

Still another aspect of the present invention provides an enzyme mixing-biomass refining apparatus comprising: (a) an extruder comprising a cylindrical housing and a rotatable screw mounted in the housing, wherein one side of the housing is connected to a feedstock feeding unit, and an outlet provided at the other side of the housing is connected to a biomass inlet of a refiner; and (b) the refiner including: a stator disc having a cooling water unit formed on the outer peripheral surface thereof, one or more enzyme feeding holes provided in a refining region thereof, and a biomass inlet provided at the central portion thereof; and a refining disc which is provided so as to form a gap with the inner surface of the stator disc and to have a refining region opposite to that of the stator disc and is rotated by a separate motor.

Yet another aspect of the present invention provides a method for simultaneously performing biomass refining and enzyme mixing, the method comprising the steps of: (a) horizontally transferring biomass by rotation of an extruder screw into a gap, formed between a stator disc of a refiner and a refining disc disposed opposite thereto, through a biomass feeding opening provided at a center of the stator disc; (b) maintaining an internal temperature of the gap, formed between the stator disc and the refining disc disposed opposite thereto, at a temperature between 40° C. and 80° C., by circulating cooling water to a cooling water space, provided on the outer peripheral surface of the stator disc; and (c) saccharifing the biomass by feeding an enzyme into one or more holes provided in a refining region adjacent to a circumference of the stator disc, and rotating the refining disc to refine the biomass while mixing the biomass with the enzyme.

EXPLANATION OF SYMBOLS

Figure 1:
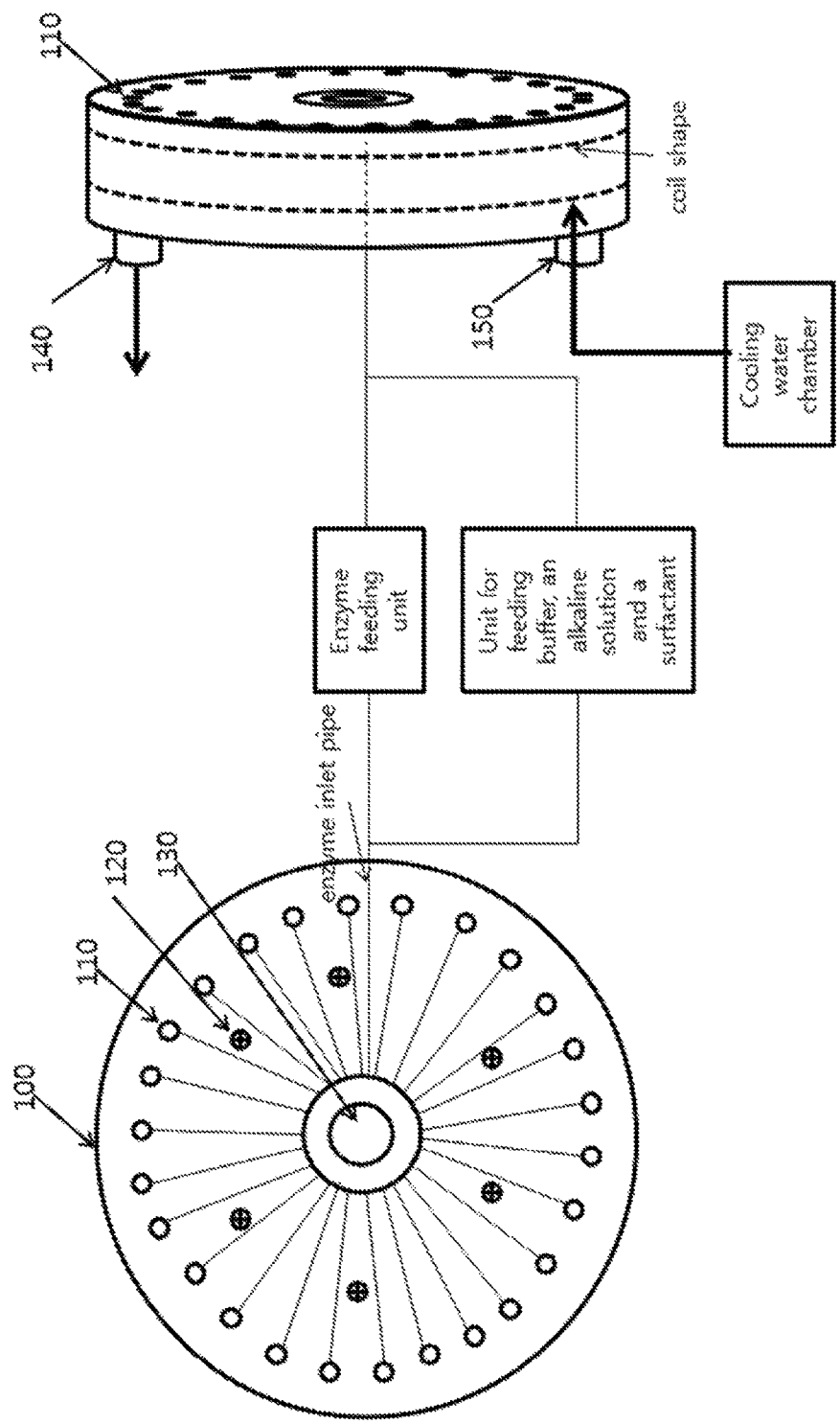
FIG. 1 schematically shows front and side views of a stator disc having enzyme feeding holes.
Figure 2:
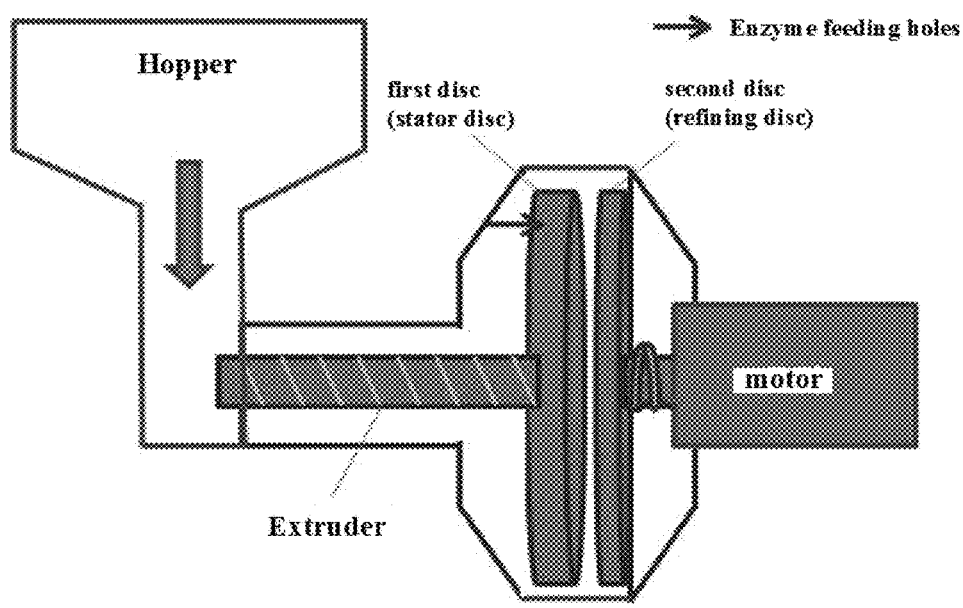
FIG. 2 is a schematic view of an enzyme mixing-biomass refining apparatus comprising a stator disc having enzyme feeding holes.

100: stator disc
110: holes
120: fixing bolt
130: biomass inlet
140: cooling water outlet
150: cooling water inlet

EMBODIMENTS

Hereinafter, embodiments of the present invention will be described in further detail.

A typical method for physical pretreatment of biomass has disadvantages in that energy consumption is high, the process proceeds slowly, and the efficiency of saccharification is low. Particularly, when an enzyme is mixed after refining of biomass having a solid content of 10-30%, there is a disadvantage in that the enzyme is not smoothly mixed by simple stirring because it is compressed during passage through a refiner.

In one example of an apparatus configured to refine biomass by feeding biomass between two rotating discs, refining and mixing can be simultaneously performed by feeding biomass between two rotating discs. But, because an enzyme is fed in a mixture with biomass, the enzyme can bind to non-refined biomass, or the thermal denaturation of the enzyme cannot be prevented.

In another example of an apparatus configured to refine feedstock by feeding the feedstock between two rotating discs, refining and the preparation of sludge can be simultaneously performed by feeding feedstock between two rotating discs while feeding liquid around the central axis. But, when an enzyme is fed to the central portion, the enzyme can bind to non-refined biomass to reduce the activity thereof, and the thermal denaturation of the enzyme and a product cannot be prevented.

Accordingly, the present inventors have made extensive efforts to develop a physical pretreatment process that reduces the use of energy and has high saccharification efficiency, and also to shorten pretreatment procedures, including biomass refining and enzyme mixing which have been individually performed, and to increase the efficiency with which the enzyme is mixed. As a result, the present inventors have developed an enzyme mixing-biomass refining apparatus comprising a cooling unit provided in a refining plate having enzyme feeding holes in order to simultaneously perform biomass refining and enzyme mixing, the cooling unit functioning to prevent the internal temperature of the plate from being increased to 100° C. or higher by frictional heat generated during refining to thereby prevent the denaturation of the enzyme. In addition, the present inventors have found that, when the enzyme mixing-biomass refining apparatus is used in a process for pretreating biomass having a solid content of 10-30%, the number of steps of the process can be reduced to reduce the consumption of energy, and particularly, the efficiency of saccharification can be increased as a result of the efficient mixing of the enzyme.

The present inventors have made extensive efforts to develop an apparatus capable of simultaneously performing biomass refining and enzyme mixing using a refiner comprising a disc having holes through which an enzyme can be fed. In addition, the present inventors have found that, when the developed apparatus is used in processes for pretreating biomass having a solid content of 10-30%, a biomass refining process and an enzyme mixing process can be simultaneously performed so as to reduce the pretreatment process time and energy consumption, and particularly, the efficiency of saccharification can be increased as a result of the efficient mixing of the enzyme.

One aspect of the present invention is directed to an enzyme mixing-biomass refining apparatus comprising: (a) an extruder comprising a cylindrical housing and a rotatable screw mounted in the housing, wherein one side of the housing is connected to a feedstock feeding unit, and an outlet provided at the other side of the housing is connected to a biomass inlet of a refiner; and (c) the refiner including: a stator disc having a cooling water unit formed on the outer peripheral surface thereof, one or more enzyme feeding holes provided in a refining region thereof, and a biomass inlet provided at the central portion thereof; and a refining disc which is provided so as to form a gap with the inner surface of the stator disc and to have a refining region opposite to that of the stator disc and is rotated by a separate motor.

In an embodiment of the present invention, the holes may be penetratingly formed in a refining region adjacent to the circumference of the stator disc, and may be connected to an enzyme inlet pipe connected to an enzyme feeding unit.

In the apparatus according to embodiments of the present invention, heat is generated when the refining disc is rotated, so that the internal temperature of the refiner may increase to cause the denaturation of an enzyme. For this reason, a cooling unit may further be disposed to the stator disc so that the stator disc can be maintained at a constant temperature that does not influence the activity of the enzyme.

If the holes are disposed adjacent to the axial center of the disc, an enzyme fed in the biomass refining process can be denatured. For this reason, the holes may be disposed at a certain distance from the axial center, and preferably, may be disposed in a refining region adjacent to the circumference of the stator disc. Biomass fed to the central portion of the stator disc is refined by the rotation of the stator disc, and the refined biomass is pushed out in the circumferential direction of the stator disc as the feedstock (biomass) is fed. If the enzyme is fed simultaneously with biomass or fed to the central portion of the stator disc, the enzyme is highly likely to be denatured by the heat and pressure of the stator disc. This denaturation is an important factor that reduces the degradation of biomass and the efficiency of saccharification. To prevent this denaturation, the pressure of the stator disc can be reduced or a cooling material can be used to remove heat generated by rotational friction. However, if the pressure of the stator disc is low, it will be difficult to refine biomass having high hardness, and if the temperature of the stator disc is low, the viscosity of the refined biomass will increase to make a normal operation difficult. For this reason, high pressure and high temperature operating conditions are required to facilitate the refining of biomass, and at the same time, the holes through which the enzyme is fed are preferably disposed in a region adjacent to the circumference of the stator disc in order to prevent the denaturation of the enzyme.

The enzyme feeding unit is a pressure pump connected to the enzyme storage tank so that the enzyme will be fed into the holes, disposed at a distance of 0.5-10 cm inward from the circumference of the refiner plate (in a direction from the circumference to the center), at a flow rate corresponding to 1-50% of the weight of biomass entering the refiner. The holes can be suitably selected depending on the treatment rate of biomass, the diameter of the plate and the solid content of biomass, and the number of the holes may be 1-12 (angular intervals of 30°), but is not limited thereto.

Meanwhile, when a cooling unit is provided to facilitate the control of the internal temperature of the refiner, one or more holes may be provided at any position in the refining region of the stator disc. Also, some of the holes may be connected to the enzyme feeding unit, and the remaining holes may be separately connected to a unit for feeding one or more additives selected from the group consisting of buffer, an alkaline solution and a surfactant.

The shape of the holes may be circular, square or polygonal, but is not limited thereto. Further, the size of the holes can be easily selected by those skilled in the art depending on the internal pressure of the refiner, the treatment capacity of the refiner, or the solid content of biomass.

The cooling unit may comprise a cooling water unit disposed on the outer peripheral surface of the stator disc to maintain the internal temperature of the refiner at a constant level.

The cooling water unit may be a single-layer coil-shaped cooling water channel, a multilayer coil-shaped cooling water channel, or a cooling water tank. Specifically, cold cooling water enters a lower inlet for cooling water and is heat-exchanged with generated heat between plates, and hot water comes out through an upper outlet for cooling water and enters a chiller again.

As used herein, the term "refining" refers to a process of reducing the size of biomass having a high solid content by the rotational force of two refining plates, and may be used interchangeably with a term such as grinding or milling.

As used herein, the term "refining disc" refers to a disc coupled to a rotating shaft, which is rotated by external power, and is rotated in the same direction as the rotating direction of the shaft. The term "refining disc" may be used interchangeably with a term such as a non-fixed refiner plate or a refiner rotor disc.

In an embodiment of the present invention, biomass that can be treated by the enzyme mixing-biomass refining apparatus may have a solid content of 10-30%.

Woody biomass generally includes cellulose, hemicellulose and lignin, even though the compositions and contents of the chemical components of wood vary depending on the kind of tree (a needle-leaf tree or a broad-leaved tree), the age of trees, etc. Thus, it is generally called "lignocelluloses", and is also called "cellulosic biomass", because it comprises polysaccharide cellulose that is the main component of the cell wall of woody or grassy biomass.

Thus, the term "biomass" as used herein may be used interchangeably with cellulosic biomass, woody biomass, lignocellulosic biomass or woody biomass.

Relevant types of biomasses for refining and mixing according to embodiments of the present invention may include biomasses derived from agricultural crops, for example, starch containing grains and refined starch; bagasse, straw from, for example, rice, wheat, rye, oat, barley, rye, rape, sorghum; softwood, for example, *Pinus sylvestris, Pinus radiate*; hardwood, for example, *Salix* spp. *Eucalyptus* spp.; tubers, for example, beet, potato; cereals from, for example, rice, wheat, rye, oat, barley, rye, rape, sorghum and corn; and the like.

In an embodiment according to embodiments of the present invention, the refiner may comprise a stator disc that does not rotate, and a rotating refining disc vertically connected to a rotating shaft fixed to an individual rotor. In an embodiment, the upper or lower portion of the housing including the discs may comprise an enzyme feeding unit, a pressure maintaining unit, an additive feeding unit, a biomass inlet connected to an extruder, a pretreated biomass outlet, and a plurality of openings to which a cooling water feeding unit may be connected, and the position and number of the openings are not limited.

In an embodiment of the present invention, the stator disc may comprise a cooling water unit on the outer peripheral surface thereof so that the internal temperature of a gap formed between the stator disc and the refining disc disposed opposite thereto can be maintained between 40° C. and 80° C., preferably 45° C. and 65° C., in order to prevent the denaturation of the fed enzyme and facilitate a saccharification reaction.

The cooling water unit may be a single-layer coil-shaped cooling water channel, a multilayer coil-shaped cooling water channel, or a cooling water tank, and the channel may be a circulating channel, a passage channel or a branched channel, but is not limited thereto.

The outlet provided in the housing of the refiner in the apparatus according to embodiments of the present invention may be connected to a next-step reactor by a pipe so that the biomass, refined and mixed with the enzyme by the apparatus, may be transferred to the next-step reactor, preferably a saccharification reactor, through the outlet.

Another aspect of the present invention is directed to a method for simultaneously performing biomass refining and enzyme mixing, the method comprising the steps of: (a) horizontally transferring biomass by rotation of an extruder screw into a gap, formed between a stator disc of a refiner and a refining disc disposed opposite thereto, through a biomass feeding opening provided at a center of the stator disc; (b) circulating cooling water to a cooling water space, provided on the outer peripheral surface of the stator disc, to maintain an internal temperature of the gap, formed between the stator disc and the refining disc disposed opposite thereto, at a temperature between 40° C. and 80° C.; and (c) feeding an enzyme into one or more holes provided in a refining region adjacent to a circumference of the stator disc, and rotating the refining disc to refine the biomass while mixing the biomass with the enzyme to saccharify the biomass.

If the temperature of step (c) is lower than 40° C., the rate of enzymatic saccharification will be low, and if the temperature of step (c) (enzymatic saccharification step) is higher than 80° C., the denaturation of the enzyme may occur. For this reason, the temperature may be between 45° C. and 65° C.

As used herein, the term "saccharification" refers to a process in which cellulose is converted to glucose by the action of an enzyme. The saccharification process can be divided into a process in which cellulose is adsorbed onto the reactive surface of cellulose to convert cellulose to cellobiose, and a process in which the produced cellobiose is converted to glucose by the enzymatic reaction of β-glucosidase.

In the method according to embodiments of the present invention, the enzyme is one or more selected from the group consisting of endo-1,3(4)-beta-glucanase, laminarinase, exo-1,2-1,6-alpha-mannosidase, alpha-N-arabinofuranosidase, feruloyl esterase, endo-1,5-alpha-arabinanase, pectinase, polygalacturonase, pectin esterase, aspartic protease, metallo protease, endo-(1,4)-mannanase, phytase, alpha-glucuronidase, beta-glucuronidase, hexenuronidase, alkaline phosphatase, acid phosphatase, alpha-galactosidase, beta-galactosidase, beta-mannosidase, and alpha-fucosidase. Preferably, the enzyme may be cellulose, β-glucosidase, hemicellulase, and/or xylanase, but is not limited thereto.

In an embodiment of the present invention, an additive other than the enzyme may further be fed into the holes. Preferably, the additive other than the enzyme may be buffer, an alkaline solution or a surfactant.

Unless otherwise defined, all technical terms and scientific terms as used herein have the same meanings as those generally understood by those skilled in the art to which the present invention pertains. In the following description and the accompanying drawings, the detailed description on known related functions and constructions will be omitted to avoid unnecessarily obscuring the subject matter of the present invention hereinafter.

The apparatus and method according to embodiments of the present invention can simultaneously perform biomass refining and enzyme mixing using a refiner including a stator disc having one or more enzyme feeding holes formed therein, and thus has the effect of reducing the pretreatment process time and energy consumption. Particularly, embodiments of the present invention enable the efficient mixing of an enzyme, and thus can increase the efficiency of saccharification in a saccharification step following the mixing step. Accordingly, embodiments of the present invention are useful for the production of cellulosic sugar and bioethanol.

What is claimed is:

1. An enzyme mixing-biomass refining apparatus comprising: (a) a cylindrical housing comprising an extruder and a rotatable screw mounted in the housing, wherein one side of the housing is connected to a feedstock feeding unit, and an outlet provided at the other side of the housing is connected to a biomass inlet of a refiner; and (b) the refiner comprising: a stator disc having a cooling water unit formed on the outer peripheral surface thereof, one or more enzyme feeding holes provided in a refining region thereof, and a biomass inlet provided at the central portion thereof; and a refining disc which is provided so as to form a gap with the inner surface of the stator disc and to have a refining region opposite to that of the stator disc and is rotated by a separate motor, wherein the biomass inlet is disposed at an axial center of the stator disc, wherein the holes are penetratingly disposed at a distance of 0.5-10 cm inward from the circumference of the stator disc in a direction from the circumference to the axial center of the stator disc, and wherein the cooling water unit maintaining the temperature of a gap formed between the stator disc and the refining disc disposed opposite thereto between 40° C. and 80° C. is disposed so as to be brought into contact with the outer peripheral surface of the stator disc.

2. The enzyme mixing-biomass refining apparatus of claim 1, wherein the holes are connected to an enzyme inlet pipe connected to an enzyme feeding unit.

3. A method for simultaneously performing biomass refining and enzyme mixing using the enzyme mixing-biomass refining apparatus of claim 1, the method comprising: (a) horizontally transferring biomass by rotation of an extruder screw into a gap, formed between a stator disc of a refiner and a refining disc disposed opposite thereto, through a biomass feeding opening provided at a center of the stator disc; (b) maintaining an internal temperature of the gap, formed between the stator disc and the refining disc disposed opposite thereto, at a temperature between 40° C. and 80° C., by circulating cooling water to a cooling water space, provided on the outer peripheral surface of the stator disc; and (c) sacchariﬁng the biomass by feeding an enzyme into one or more holes provided in a refining region adjacent to a circumference of the stator disc, and rotating the refining disc to refine the biomass while mixing the biomass with the enzyme.

4. The method of claim 3, wherein an additive other than the enzyme is further fed into the holes of the step of (c).

5. The method of claim 3, wherein the enzyme is one or more selected from the group consisting of endo-1,3(4)-beta-glucanase, laminarinase, exo-1,2-1,6-alpha-mannosidase, alpha-N-arabinofuranosidase, feruloyl esterase, endo-1,5-alpha-arabinanase, pectinase, polygalacturonase, pectin esterase, aspartic protease, metallo protease, endo-(1,4)-mannanase, phytase, alpha-glucuronidase, beta-glucuronidase, hexenuronidase, alkaline phosphatase, acid phosphatase, alpha-galactosidase, beta-galactosidase, beta-mannosidase, and alpha-fucosidase.

6. The method of claim 4, wherein the additive is buffer, an alkaline solution or a surfactant.

7. The method of claim 3, wherein the biomass has a solid content of 10-30%.

* * * * *